(12) United States Patent
Tse

(10) Patent No.: US 6,469,513 B1
(45) Date of Patent: Oct. 22, 2002

(54) AUTOMATED STATIONARY/PORTABLE TEST SYSTEM FOR APPLYING A CURRENT SIGNAL TO A DIELECTRIC MATERIAL BEING TESTED

(75) Inventor: Ming-Kai Tse, Lexington, MA (US)

(73) Assignee: Quality Engineering Associates, Inc., Burlington, MA (US)

( * ) Notice: Subject to any disclaimer, the term of this patent is extended or adjusted under 35 U.S.C. 154(b) by 0 days.

(21) Appl. No.: 09/309,104

(22) Filed: May 10, 1999

Related U.S. Application Data

(63) Continuation-in-part of application No. 08/770,996, filed on Dec. 23, 1996, now Pat. No. 5,929,640, which is a division of application No. 08/040,770, filed on Mar. 31, 1993, now abandoned, which is a continuation of application No. 07/975,380, filed on Nov. 12, 1992, now abandoned.

(51) Int. Cl.[7] .............................................. G01N 27/60
(52) U.S. Cl. ........................ 324/455; 324/456; 324/554
(58) Field of Search ................................ 324/455, 452, 324/551, 554, 456

(56) References Cited

U.S. PATENT DOCUMENTS

| | | | |
|---|---|---|---|
| 2,856,582 A | 10/1958 | Anderson | 324/61 |
| 3,523,246 A | 8/1970 | Hall et al. | 324/61 |
| 3,544,889 A | 12/1970 | Alauzet et al. | 324/32 |
| 3,727,125 A | 4/1973 | Mourier | 324/32 |
| 3,970,920 A | 7/1976 | Braun | 324/32 |
| 4,233,562 A | * 11/1980 | Blythe | 324/455 |
| 4,443,764 A | 4/1984 | Suh et al. | 324/456 |
| 4,613,228 A | 9/1986 | Suzuki et al. | 355/14 R |
| 4,780,680 A | 10/1988 | Reuter et al. | 324/455 |
| 4,885,543 A | 12/1989 | Smith | 324/452 |
| 5,101,159 A | 3/1992 | Bossard et al. | 324/456 |
| 5,117,191 A | * 5/1992 | Saigo et al. | 324/551 |
| 5,119,030 A | 6/1992 | Bossard et al. | 324/456 |
| 5,175,503 A | 12/1992 | Mishra et al. | 324/452 |

OTHER PUBLICATIONS

Brochure, *"Trek Photoreceptor Analysing System, Model Elysia–I"*. (No date).
*"Trek Introduces a New Era in Photoreceptor Testing"*, Trek, Inc., Medina, New York, 1991.
Brochure, *Gentec, "Cynthia 90"*. (No date).
M. Tse et al., *"An Electrostatic Charge Decay Technique for Nondestructive Evaluation of Nonmetallic Materials"*, Laboratory for Manufacturing and Productivity, MIT School of Engineering, Cambridge, MA, (No date).

\* cited by examiner

Primary Examiner—Walter E. Snow
(74) Attorney, Agent, or Firm—Weingarten, Schurgin, Gagnebin & Lebovici LLP

(57) ABSTRACT

An automated test system is provided for evaluating characteristics of photoreceptors used in the electrophotographic process. The test system includes a dielectric material support adapted to receive said dielectric material one or more electrodes adapted to apply electrical energy from a source to a two dimensional area adjacent the support for storage by the dielectric material and a sensor for the electrical energy stored in the dielectric material and providing an output representation of the dielectric relaxation of the material in response to the stored energy over the two dimensional area. This test system provides advantages over conventional Electrostatic Charge Decay (ECD) methods by eliminating corona pre-charging and a moving detector when a full-length array is used. Also, this test system utilizes a lower cost current detector in comparison to conventionally used voltage detectors.

8 Claims, 13 Drawing Sheets

Substrate Cleanliness Evaluation Setup

Axial Position
- Initial: 0.500 inch
- Final: 10.500 inch
- Increment: 0.039 inch/rev Rotational Speed: 2.00 revs/sec
Charger Voltage: 5.000 kV
Sample Spacing: 0.037 inch

Charger Polarity
- ○ Positive
- ⊙ Negative

☐ Corotron ON

[Load] [Help]
[Save] [OK]

*FIG. 3*

Layer Thickness Measurement Setup

Axial Position
- Initial: 0.500 inch
- Final: 10.500 inch
- Increment: 0.039 inch/rev Rotational Speed: 2.00 revs/sec
Charger Voltage: 6.000 kV
Sample Spacing: 0.037 inch

Charger Polarity
- ○ Positive
- ⊙ Negative

Layer
- ○ Base
- ⊙ Charge Generation

Discharge Light
☐ White
Relative Intensities
- Red (635 nm) 0 (0-100)
- Green (565 nm) 0 (0-100)
- Blue (470 nm) 0 (0-100)

[Help] [Load] [Save] [OK]

*FIG. 5*

AUTOMATED STATIONARY/PORTABLE TEST SYSTEM FOR APPLYING A CURRENT SIGNAL TO A DIELECTRIC MATERIAL BEING TESTED

CROSS-REFERENCE TO RELATED APPLICATIONS

The instant invention is a continuation-in-part of commonly-assigned patent application Ser. No. 08/770,996, filed Dec. 23, 1996 (issued as U.S. Pat. No. 5,929,640) which is a division of commonly-assigned patent application Ser. No. 08/040,770, filed Mar. 31, 1993 which is a continuation of commonly-assigned patent application Ser. No. 07/975,380, filed Nov. 12, 1992 (now abandoned).

FIELD OF THE INVENTION

The invention relates to methods for nondestructive evaluation of materials and more particularly to tests for photoreceptors.

BACKGROUND OF THE INVENTION

A key component in many copy machines and laser printers is a photoreceptor onto which a powdered "ink" or toner is deposited in a precise pattern. The pattern is generated by light exposure, and corresponds to the images or letters to be copied or printed. Paper is placed into contact with the photoreceptor, toner is transferred to the paper, and the "inked" paper is subjected to heat and pressure to fuse the toner onto the paper. The photoreceptor is then wiped clean of any remaining toner, and the process is repeated.

Among many possible configurations, an important commercial photoreceptor design is a multilayer structure wherein a metal drum is coated with an insulating polymer base layer, and an organic photoconductive (OPC) overcoat consisting of a charge generating layer and a charge transport layer. In the copying or laser printing process, deposition of the toner on the photoconductive drum is effected by creating a negatively or positively charged pattern on the drum to which oppositely charged particles of toner powder cling. This initial charged pattern is created by imparting a charge of the desired polarity to the entire drum. After electrostatic charging, the cylinder is carefully exposed to a pattern of light which causes charge carriers to be freed within the charge generating layer of the drum. These charge carriers, under the influence of the existing electric field, migrate through the charge transport layer, neutralize the deposited charge, thereby electrically discharging those portions. The remaining charged portions of the surface correspond to the pattern to which the toner is electrostatically attracted.

To produce clear and consistent images, the photoconductive drum must be able to consistently accept a sufficient level of charge, hold the charge for a sustained period of time in the dark, and discharge rapidly under controlled light exposure over repeated cycles. Devices presently exist which enable tests of certain charge build-up, charge retention, and discharge characteristics to be performed. However, these devices are not suitable for measuring other quality characteristics during the manufacture of new drums, or in the recycling of used drums. These characteristics include the cleanliness of the underlying metal drum surface, the uniformity of thickness of the polymer base and charge generation layers, the presence of layer defects, and various measures of electrophotographic performance across the entire drum surface.

While generalized techniques for nondestructive detection and characterization of flaws in materials, such as those described in U.S. Pat. No. 4,443,764 to Suh et al. are known, there is no automated test apparatus or series of tests that is capable of evaluating the full range of photoconductive drum characteristics that bear on print quality. Such tests and an easily operated apparatus for performing them would be important to quality control during manufacture and refurbishment of products having photoconductive drums.

Other materials such as paper and other media may be called upon to hold a charge and a system is needed for their testing as well with out expensive and time consuming procedures.

SUMMARY OF THE INVENTION

The present invention provides a fully automated test system capable of performing a comprehensive series of tests to evaluate the numerous characteristics of the various layers of a photoreceptor, such as a photoconductive drum, which affect its print performance. The tests include complete electrophotographic characteristic evaluation, defect mapping, layer thickness measurement and uncoated drum substrate cleanliness testing.

The user can select and test for the cleanliness of the uncoated drum surface; the thickness of the drum's base coating polymer (with or without a charge generating layer thereon) and of the charge generating layer itself; the presence of defects in the base, charge generating, transport layers; as well as the charge build-up, charge retention and discharge characteristics of the completed drums.

A further feature of the invention is a test system including a control unit responsive to user defined parameters for controlling preprogrammed tests; a test station including a drum retainer for holding and rotating the drum, a charging system having a high voltage power supply and a polarity selector, a light source for causing localized electrostatic discharge, a broad spectrum light source for causing global electrostatic discharge, and a low voltage and a high voltage non-contact electrostatic surface potential probe; a light-proof cabinet for enclosing the test station; an adjustable fixture for the charging system, high voltage and low voltage probes and electronics therefor for drum scanning, a mounting ring to provide convenient positioning and adjustment of the probes and light source; and motors to produce drum rotation and ring movement; and an output device for presenting test results to a system operator.

The drum substrate surface cleanliness test includes completely scanning the drum by the low voltage electrostatic sensor to measure contact potential values or the surface potential on the surface of the drum to detect surface contamination.

The layer thickness test can be run on a drum having a base polymer layer with or without the charge generating layer thereon. By appropriate use of charge polarity and discharge light, the thickness of each layer is determined from the differences in charge mobility and photosensitivity of the two layers.

The defect test is typically run on a fully layered drum. The drum is charged during a scan and the resulting potential on the drum surface is immediately measured. In this test, different combinations of test conditions including the light exposure level and charge polarity provide indications of different types of defects.

The electrophotographic measurement test is conducted on a fully layered drum. The system continuously monitors the potential on the drum surface at a predefined set of locations while sequentially performing each of the following operations for a predefined time duration: imparting an electrostatic charge to the drum; allowing the charge to decay in the dark; and finally illuminating at least a portion of the drum surface with light of a preselected wavelength and intensity to cause electrostatic discharge. Parameters which characterize the electrophotographic performance of the drum are obtained and/or computed from the acquired data. The entire test sequence is repeated many times to perform a cyclic fatigue test of the drum.

A further feature of the invention is a test system including a charging device, a voltage measurement probe, and a light source that are conveyed linearly along a photoconductive drum for performing voltage acceptance and discharge testing.

Yet another feature of the invention is a life-cycle test for comparing voltages imparted to a drum and residual voltages after discharge by a light source to life-cycle reference voltages for a similar drum.

In other features of the invention, embodiments are provided for the testing of substrates in the nature of paper and other media, for testing both voltage retention and current acceptance, and for the dielectric relaxation process. Corona electrodes or capacitive arrays, rollers and wires are utilized for applying electrical test energy.

BRIEF DESCRIPTION OF THE DRAWINGS

These and further features of the invention can may be better understood with reference to the accompanying specification and the drawings in which:

FIG. 3 is a depiction of a parameter selection display for the substrate cleanliness test of FIG. 2, provided by the user interface of the control software for the control unit of FIG. 1;

FIG. 5 is a depiction of a parameter selection display for the layer thickness measurement test of FIG. 2, provided by the user interface of the control software for the control unit of FIG. 1;

DETAILED DESCRIPTION OF THE INVENTION

Figure 1A:
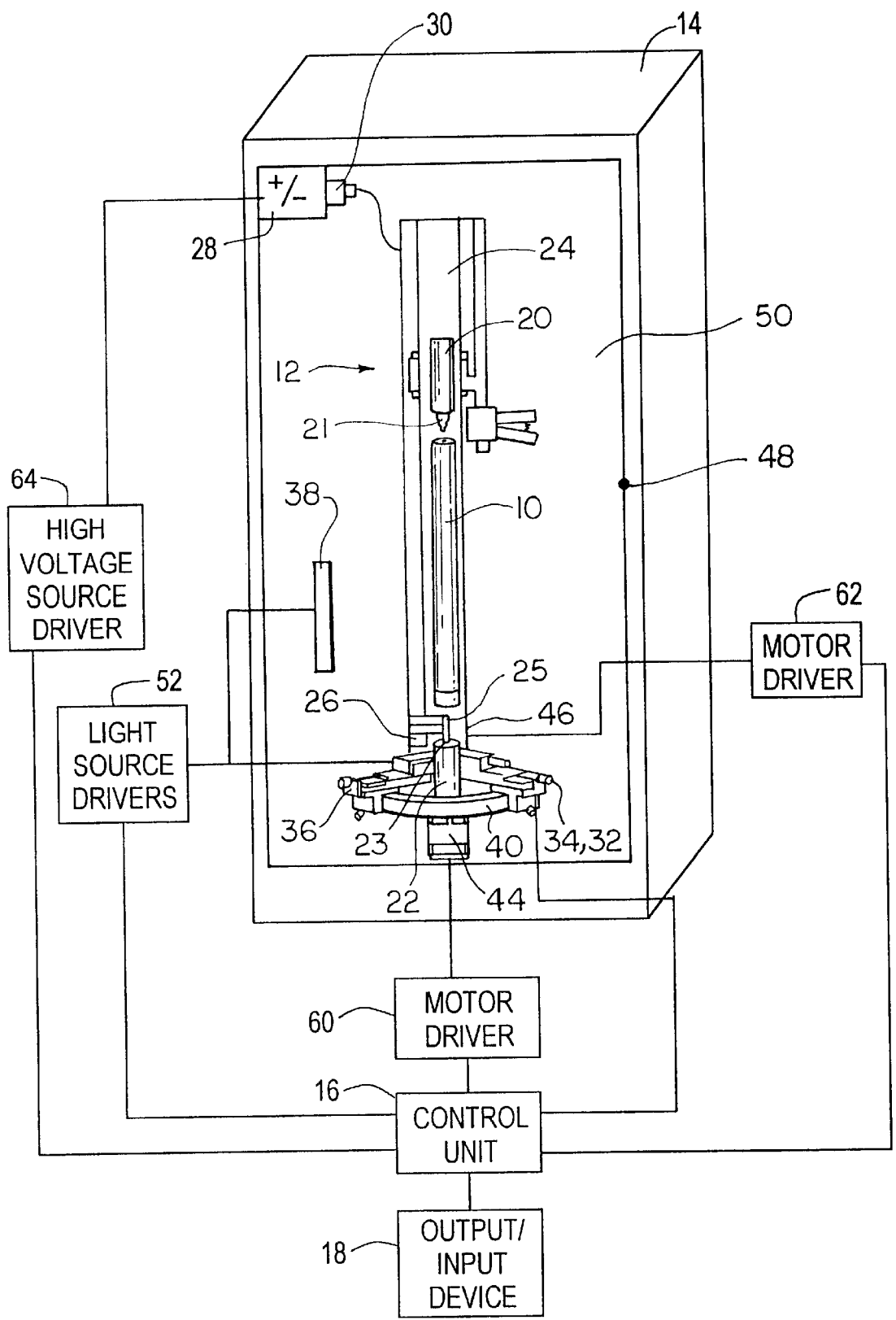
FIG. 1A is a schematic of a test system used to evaluate a photoreceptor.

FIG. 1A is a schematic of a test system used to perform nondestructive inspection and testing of thin dielectric coatings of photoreceptors used in electrophotography, such as an organic photoconductive drum 10 having a metallic core coated with a polymer base layer, a charge generating layer, and a charge transport layer. The test system includes a test station 12 located within a light-proof cabinet 14, a control unit 16, and one or more input/output devices 18.

The test system is uniquely able to integrate several test functions for the photoreceptor, a charge generating layer, a base layer, and an uncoated drum in a single, fully-computerized system. These test functions evaluate the quality characteristics that are most critical to the performance, re-usability and longevity of the drum 10. Although the focus of the ensuing description is directed toward photoconductive drums, substantially the same process and equipment can be used for other photoreceptor geometries, such as belts and flat plates.

Evaluations performed by the test system include: 1) surface cleanliness of an uncoated drum substrate; 2) thickness and uniformity of a thin polymer base layer and a charge generation layer; 3) physical defects on a new or recycled drum 10; and 4) electrophotographic performance of a new or recycled drum 10. Each of the tests can be performed over repeated cycles without conducting any or all of the other tests.

In an exemplary embodiment of the hardware components depicted in FIG. 1A, the test station 12 has a drum retainer comprising tapered upper and lower spindles, 20 and 22 respectively, that are adapted to position the drum 10 for testing and electrically ground the metallic substrate of the drum 10. The lower spindle 22 is in a fixed position with respect to the test station and is insertable into either of the hollow ends of drum 10. The lower spindle is equipped with a cone 23 partially plated with a noble metal, such as gold, that serves as a reference electrode, and a mushroom shaped positioning aid 25 that supports the drum 10 in near axial alignment with the upper spindle 20. The upper spindle 20 is slidably retained on a track 24 and is also insertable into either of the hollow ends of the drum 10. The upper spindle 20 is also equipped with a positioning cone 21 for axial alignment of the drum 10. Prior to conducting tests, a first end of the drum 10 is placed onto the lower spindle 22, after which the upper spindle 20 is lowered into engagement with the opposite end of the drum 10. When the drum 10 has end-caps, such as those used for re-manufacture of cartridges, the upper and lower positioning cones, 23 and 21 respectively, are replaced with fittings adapted to correctly position the drum 10 and to provide an electrical ground connection to the metallic substrate of the drum 10. In another embodiment, fixed-location adapters are used to position and retain photoreceptors of different sizes and types in lieu of the movable upper spindle 20. In each of the embodiments, an automatic, motorized system is optionally incorporated for positioning the upper spindle 20 or fitting to hold and release the upper end of the drum 10.

Typically, the test station 12 is configured to accommodate a drum 10 up to 400 mm long and having an 80 mm outer diameter (O.D.), however, other drum sizes can also be accommodated. The entire test station is housed in the light-proof cabinet 14 which measures approximately 18"× 24"×34" in one embodiment. It should be noted that although the test station 12 and drum 10 are depicted in a vertical orientation, other orientations such as horizontal are equally functional and compatible with the concept of the invention.

Various instrumentation to perform and monitor tests are placed within cabinet 14 including: a charging device 26, such as a scorotron, a corotron, or a roller charger energized from positive or negative high voltage power sources 28, the polarity of which is selected by a polarity selection switch 30 which is software controlled. A low voltage, non-contact, electrostatic surface potential probe 32, or a high voltage, non-contact, electrostatic surface potential probe 34; and a first light source 36 for discharging a localized portion of the drum 10 are positioned on a carrier ring 40 to face the drum 10 as it is rotated. A second light source 38 for global discharge of the drum 10 is positioned on a wall of the light-proof cabinet. The high voltage probe 34 performs measurement in the KV range, or alternatively the low voltage probe 32 can be used to measure charge in the mV to V range. Normally, the low voltage probe 32 is used for the cleanliness test and the high voltage probe 34 is used for all of the other tests. The carrier ring 40 and the instrument mounting can be adapted to easily retract from the drum 10 to facilitate loading and unloading of the drum 10 and to preclude interference with end-caps on a drum so equipped.

While the first light source 36 which causes localized discharge of the drum 10 can be selected from a variety of known light sources, such as a laser diode, a multi-wavelength (red-green-blue) LED is especially useful for providing a quick assessment of the drum's sensitivity. The selection of wavelength is related to the wavelength used to discharge the drum 10 in specific applications. In an alternative configuration, selection of wavelength is accomplished by providing a bandpass color filter through which light from a broad spectrum source, such as a tungsten or halogen lamp, is projected. Neutral density filters are provided for adjusting light intensity and a shuttering mechanism provides a means for controlling exposure time. The second light source 38 used for discharging the entire drum 10 is a high-performance fluorescent lamp or an array of light emitting diodes.

Figure 1B:
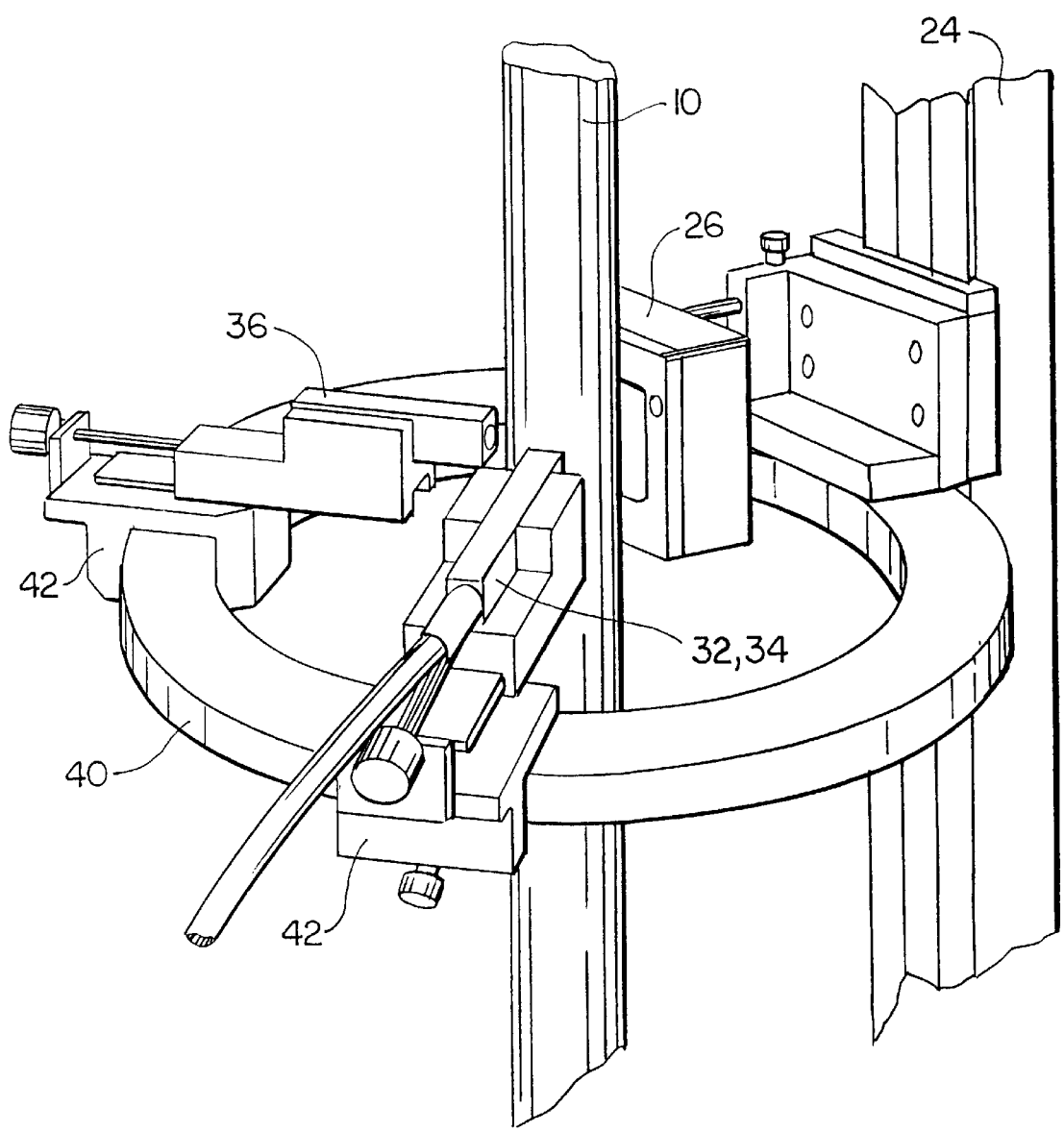
FIG. 1B is a perspective view of instrumentation used in the test system of FIG. 1A.

Referring to FIG. 1B, the charging device 26, one or more voltage probes 32,34 and one or more broad spectrum light sources 36 are mounted on circular carrier 40 via adapters or holders 42.

A first stepper motor 44 is coupled to the lower spindle 22 and enables the drum 10 mounted thereon to be variably rotated over a range of 0.1 to 5 revolutions per second with an angular resolution for drum rotation of 0.225°. A second stepper motor 46 is coupled to the carrier 40 to enable the carrier and the instrumentation thereon to be moved axially on the track 24. The axial scan speed is variable over a range of approximately 0.25 to 127 mm per second (0.01 to 5 inch per second) and the axial scan range is approximately 50 cm (20"), with a minimum step size of 0.0381 mm (0.0015"). As a result, the instrumentation carrier 40 can scan past all of the useable surface of the drum. It should be noted that most of the drum motion parameters can be modified and extended if necessary. As a safety feature, an electromechanical interlock 48 is provided on the light-proof cabinet 14 to prevent the high voltage power supply 28 from energizing when the cabinet door 50 is opened.

FIG. 1B is a perspective view of a portion of the test station 12 wherein the carrier 40 is located at an intermediate location on the track 24 and illustrates an embodiment of instrument positioning on the carrier 40. In this view, the first light source 36, the charging device 26, and the electrostatic probes 32, 34 are shown in proximity to, but not in contact with the drum 10.

All motion and scan operations of the test station are controlled by the control unit 16, typically a microcomputer which interfaces with the instrumentation including: light source drivers 52, motor drivers 60 and 62, and a high voltage source driver 64. The control unit 16 interfaces with the system operator via one or more output/input devices 18 such as a video monitor, printer, a keyboard and the like.

Figure 2:
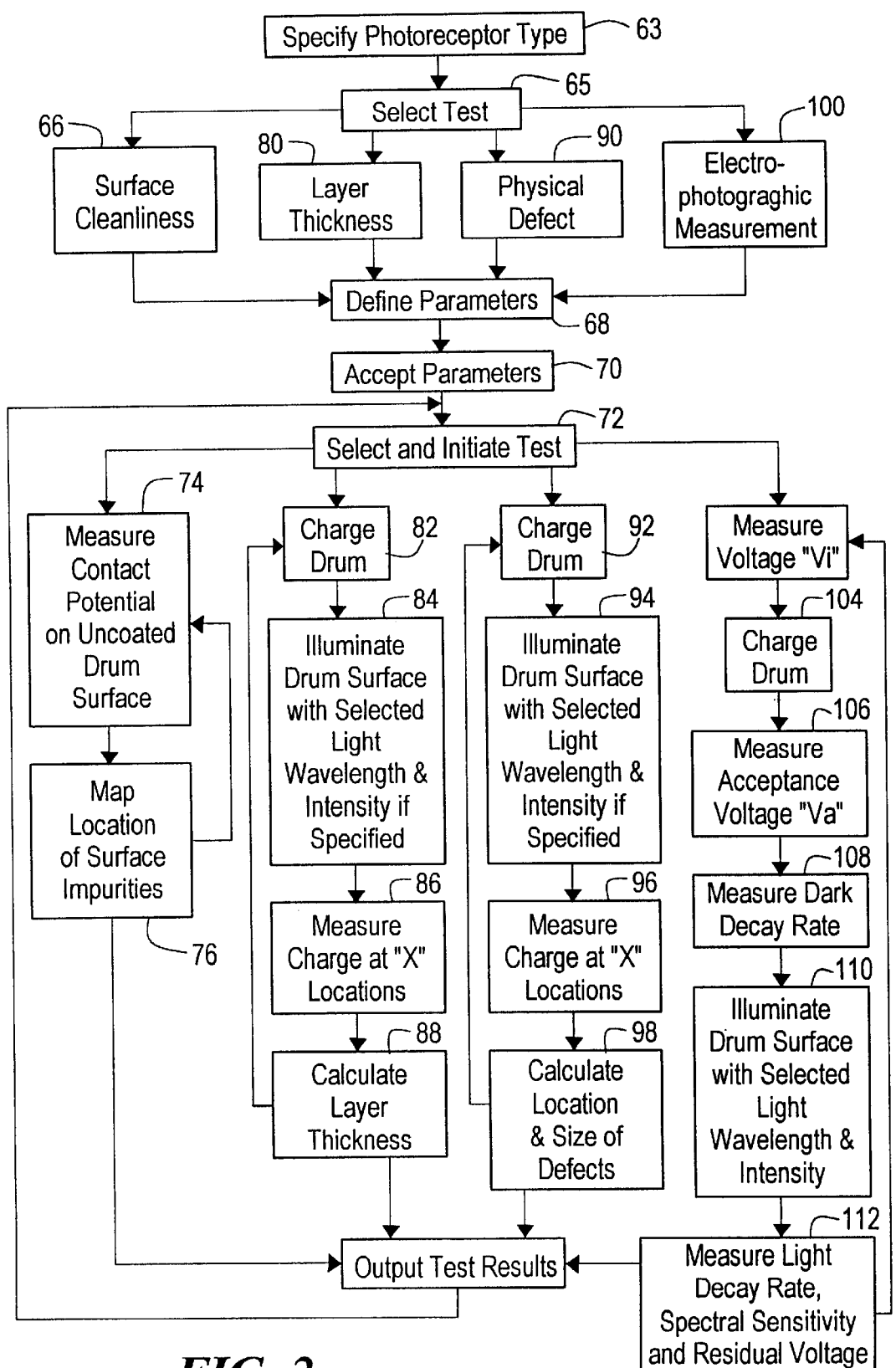
FIG. 2 is a flow-chart of user selected computer controlled tests performed by test system of FIG. 1, that are coordinated and analyzed by a control unit.

Software used by the control unit 16 to run the comprehensive series of tests may be written for a graphical user interface such as Microsoft Windows (registered trademark of Microsoft Corporation). The software allows any of the built-in tests to be performed at will using a wide range of test parameters. The software is also readily expandable to permit customized testing. For each of the software controlled tests, data is sampled from one of the probes at a fixed rate throughout the scanning procedure. After the data have been acquired, key parameters are calculated. It should be noted that the characteristics discussed hereinbelow are merely exemplary and the software may easily be altered to suit user requirements. FIG. 2 is a flow-chart of user selected tests performed by the test system of FIG. 1A using the software, and should be referred to in conjunction with the description of the various tests associated with FIGS. 3–10.

Each of the tests are fully computer-controlled and can be performed for both research and development and manufacturing quality control purposes. For research and development testing, the charge and discharge characteristics of the photoreceptor provide a direct measure of the functional performance of a specific coating formulation. For quality control evaluation, the system operator can select predefined tolerance limits to determine the acceptability of a finished product or a recycled drum.

From a main menu state the system operator specifies the photoreceptor type to be tested in step 63, followed by selecting the tests to be performed in step 65 which may include any or all of tests for: substrate surface cleanliness 66; layer thickness 80; physical defect 90; or electrophotographic performance 100.

Selecting the test for substrate surface cleanliness 66 tests the photoreceptor for the presence of surface contaminants that would interfere with the adhesion or operation of the base layer and the photoconductive layer applied to the conductive metal, typically aluminum, drum.

The cleanliness test begins, as do all of the tests, by having the system operator define the test parameters through the FIG. 3 interface in a step 68. For the cleanliness test, which may be performed on the uncoated metal drum or any conducting surface, these parameters include an initial sample situs, a final sample situs, an intermediate sample spacing increment, a sampling speed, and the option of charging on/off and charging polarity.

FIG. 3 is a depiction of a parameter selection display for an exemplary substrate cleanliness test 66, wherein the exemplary initial axial position of the low voltage probe 32 mounted on the carrier 40 is user set to 0.500 inches from a reference point, such as an end of the drum 10. The final axial position is user set to 10.500 inches from the reference point. The carrier 40 is user commanded to move along the track 24 by the second step motor 46 in increments of 0.039 inches per drum revolution, and the drum 10 is user set to be rotated by the first motor 44 at a speed of 2.00 revolutions per second. Sample measurements are user specified to be taken in 0.037 inch increments. The charging device 26 is not activated. After making any corrections to the parameters, the system operator accepts the parameters in a step 70 by clicking on "OK" and initiates the cleanliness test in a step 72, causing in turn the measurement and calculating steps 74 and 76 to be run.

Figure 4:
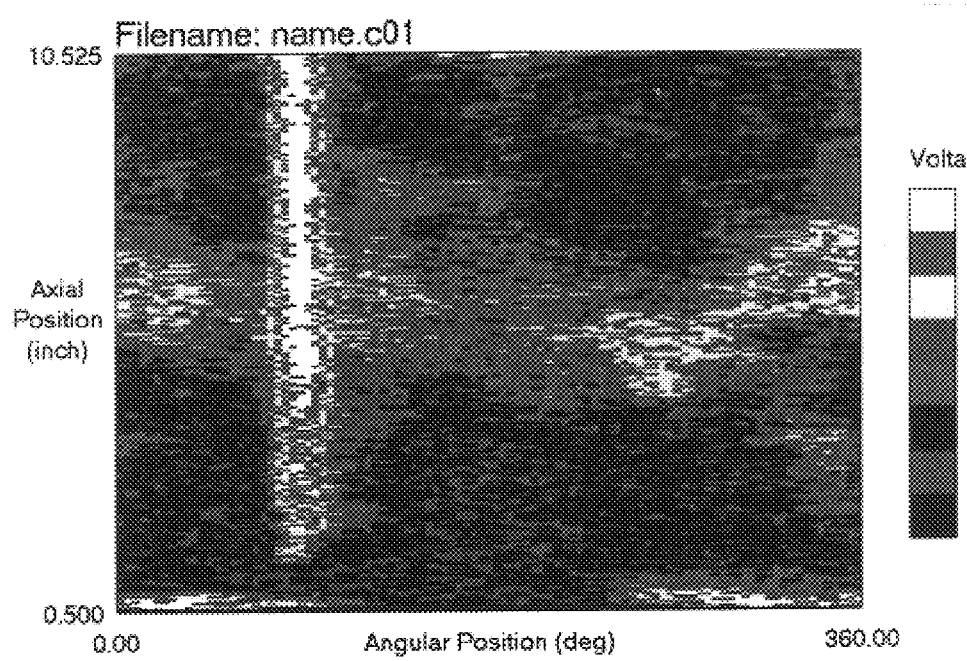
FIG. 4 is a graphical representation of the results of the substrate cleanliness test of FIG. 2.

When the cleanliness test 66 is initiated, the carrier 40 and drum 10 begin their programmed movements. The low voltage electrostatic probe 32 is scanned over the surface of the drum 10 and the voltages detected are representative of contact potential values in step 74 and these are used to calculate the degree and location of detrimental contaminants such as fingerprints or other organic/inorganic films, with the test results presented in step 78 on an output device 18 or stored for future reference, such as life-time tracking of individual photoreceptors. FIG. 4 is an exemplary screen display, which may be gray scale but is normally colored to improve discrimination of regions on the cleanliness map for the entire drum surface. At the completion of the cleanliness test the system returns to the menu state 65 so that another test can be performed.

The test system is also used to perform a layer thickness test entailing step 80, wherein an individual coating layer thickness and uniformity, such as the base layer and or the charge generation layer are evaluated. This test begins by user defining of test parameters in step 68, through the user interface of FIG. 5 and includes an initial sample situs, a final sample situs, an intermediate sample spacing increment, a sampling speed, an electrostatic charge level, and an electrostatic charge polarity. Additional parameters defined for the layer thickness test in step 68 include the layer to be tested, discharge light wavelength(s), and light intensity for purposes described below.

In FIG. 5 the initial axial position of the carrier 40 is 0.500 inches from a reference point. The final axial position is 10.500 inches from the reference point. The carrier 40 is commanded to move along the track 24 in increments of 0.039 inches per drum revolution, and the drum 10 will be rotated at a speed of 2.00 revolutions per second. Sample measurements will be taken in 0.037 inch increments. The charging device 26 is set at a 6.000 kV charging voltage.

When the system operator accepts the parameters in a step 70 and initiates the layer thickness test of steps 82–88, the drum 10 is charged. The charging device 26, such as a corotron, charges a small portion of the drum, which is then optionally illuminated, and then the probe measures the residual voltage. This process is continuous while the drum rotates and the carrier 40 moves so that the entire drum surface is passed over by the charging device 26 as indicated in step 82. The drum surface is optionally illuminated in step 84, and the carrier 40 and drum 10 make their programmed movements while the probe takes measurements of the residual charge over the defined whole or portion of the drum 10 at the preselected increments. Quantitative values of thickness are estimated and based on a predetermined calibration curve, and a distribution map of layer thickness is calculated in step 88 and output in step 78 in a desired form for the system operator.

The layer thickness test 80 can be run on a drum 10 with the base polymer with or without the charge generating layer by appropriate selection of charging device polarity and light discharge.

To measure the thickness of a base layer without another layer thereon, either a positive or a negative charge can be applied in step 82 to the drum 10 by the charging device 26. Scanning the surface of the drum 10 to measure, in step 86, the residual charge held by the layer after a passage of time, allows its thickness to be calculated as previously described in step 88.

To test the thickness of the base layer and charge generating layer when both have been applied onto the drum 10, a positive charge is used. Because the charge generating layer will hold a positive charge, the thickness of the base and charge generation layers can be calculated in step 88 by evaluating its charge decay without illumination in step 84.

The thickness of the base and charge generating layers are separately determinable by using a negative charge, and running step 84 to discharge the charge generation layers leaving the base layer charged. The thickness calculated for the base layer is subtracted from the combined layer thickness to determine the thickness of the charge generating layer.

Figure 6:
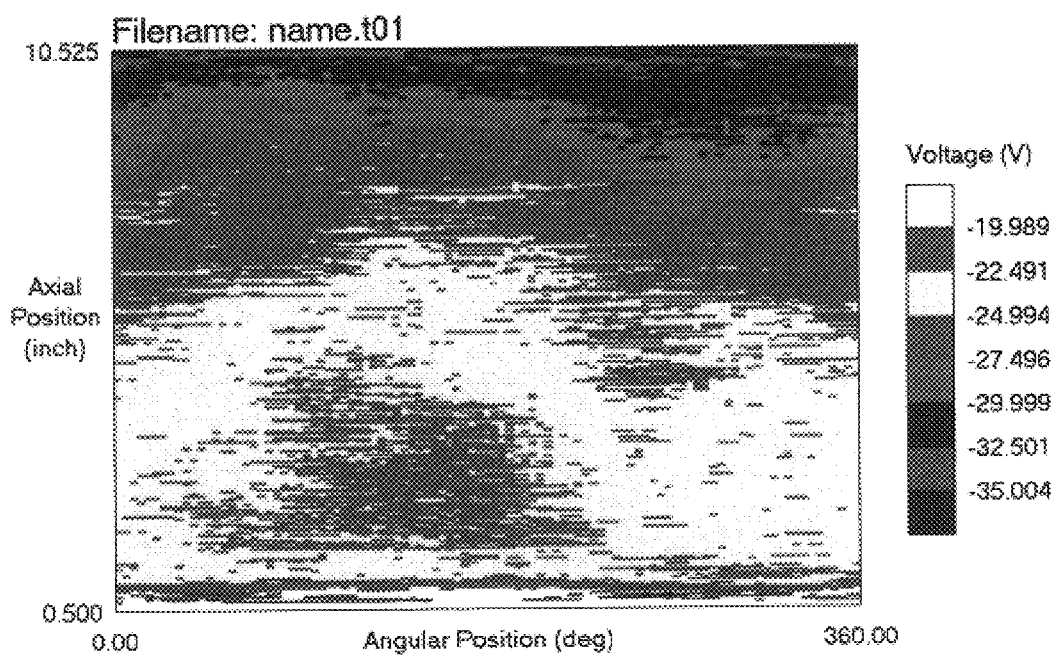
FIG. 6 is a graphical representation of the results of the layer thickness measurement test of FIG. 2.

FIG. 6 is an exemplary screen display of layer thickness map of the entire drum 10. At the completion of the layer thickness measurement, the system returns to the main menu in state 65 so that another test of the drum 10 can be performed.

In another test, the test system detects localized physical defects such as pin-holes or scratches, or distributed defects such as wear marks, non-uniform coating thickness, or poor dispersion of the light-sensitive dye, on the drum surface which can affect the quality of a print in electrophotography. The physical defect test begins by having the system operator enter the test in step 90 from state 65. Many of the same test parameters as the layer thickness test are defined in step 68, by reference to FIG. 7, namely an initial sample situs, a final sample situs, an intermediate sample spacing increment, a sampling speed, an electrostatic charge level, an electrostatic charge polarity, and discharge light wavelengths and intensities.

Figure 7:
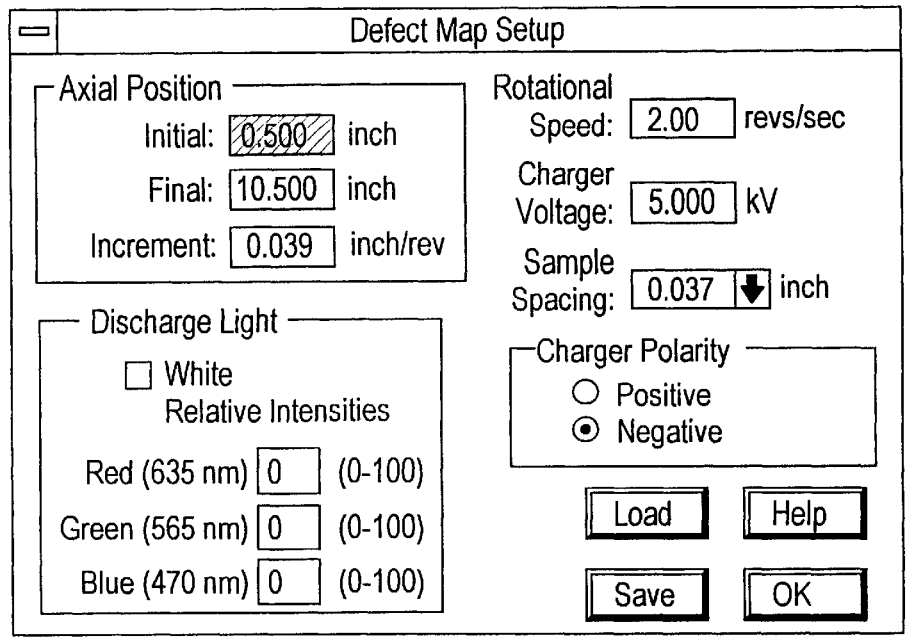
FIG. 7 is a depiction of a parameter selection display for the defect mapping test of FIG. 2, provided by the user interface of the control software for the control unit of FIG. 1.

FIG. 7 depicts a parameter selection display for an exemplary defect mapping test, wherein the initial axial position of the high voltage probe 34 is 0.500 inches from a reference point. The final axial position is 10.500 inches from the reference point. The carrier 40 is commanded to move along the track 24 in increments of 0.039 inches per drum revolution, and the drum 10 will be rotated at a speed of 2.00 revolutions per second. Sample measurements will be taken in 0.037 inch increments. The charging device 26 is set at a 5.000 kV charging voltage. After making any corrections to the parameters, the system operator accepts them in step 70, and initiates the test in step 72.

When the defect mapping test is initiated, the charging device 26 imparts in step 92 the selected charge to the drum surface, optionally in step 94 followed by illuminating at least a portion of the drum surface with the selected light source 36 to see how well the drum 10 holds a charge or discharges. The carrier 40 and drum 10 begin their programmed movements directly after charge up while the probe 34 takes measurements over the defined surface in step 96 of the held or residual charge on the drum 10 at the preselected increments. By detecting charge irregularities over a known time interval as the drum 10 rotates and instruments move, the location and size of defects are calculated 98, and a defect map can be created and output 78 to the system operator.

Figure 8:
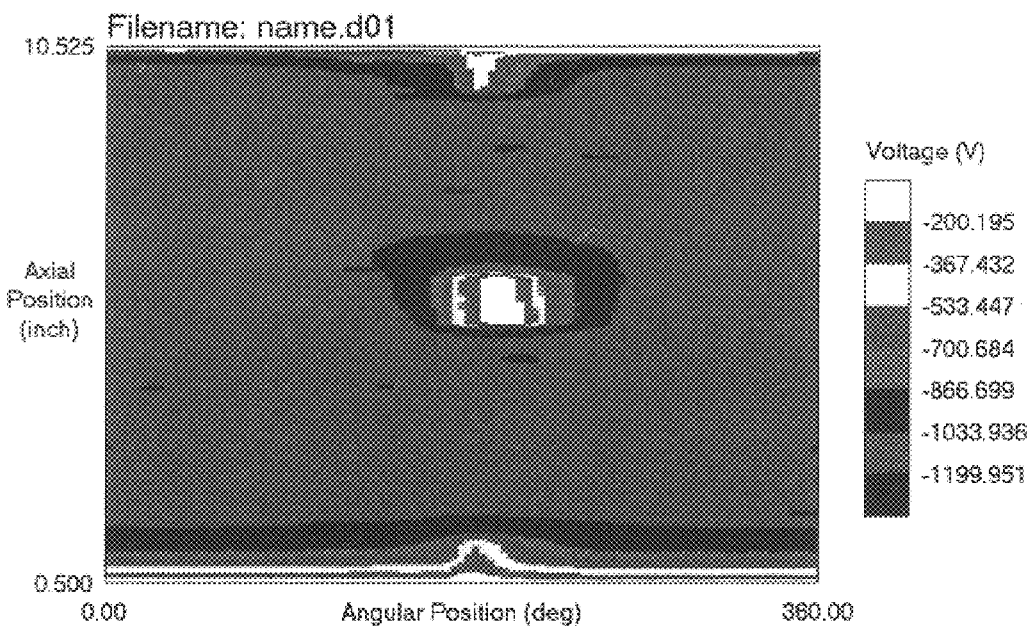
FIG. 8 is a graphical representation of the results of the defecting mapping test of FIG. 2.

For the embodiment illustrated, the spatial resolution of the defect mapping test is approximately 0.010 inch. FIG. 8 is an exemplary screen display of a defect map of the entire drum 10, which indicates a localized defect. At the completion of the defect mapping test the system returns to the main menu state 65 so that another test can be performed.

The test system can also be used to test electrophotographic performance on a fully layered new or recycled drum 10. The electrophotographic measurement test comprises several critical functional tests on the drum 10 including charge acceptance, dark decay rate, light decay rate, residual voltage, spectral sensitivity, and cyclic fatigue. This test begins by selection from the menu in step 100 and defining in step 68 test parameters including an initial sample situs, a final sample situs, a number of intermediate sample locations, a rotational speed, an electrostatic charge level, an electrostatic charge polarity, and discharge light wavelength(s) and intensities.

The parameters also include time intervals for charge, dark decay, light decay, and number of cycles and cycles between samples.

Figure 9:
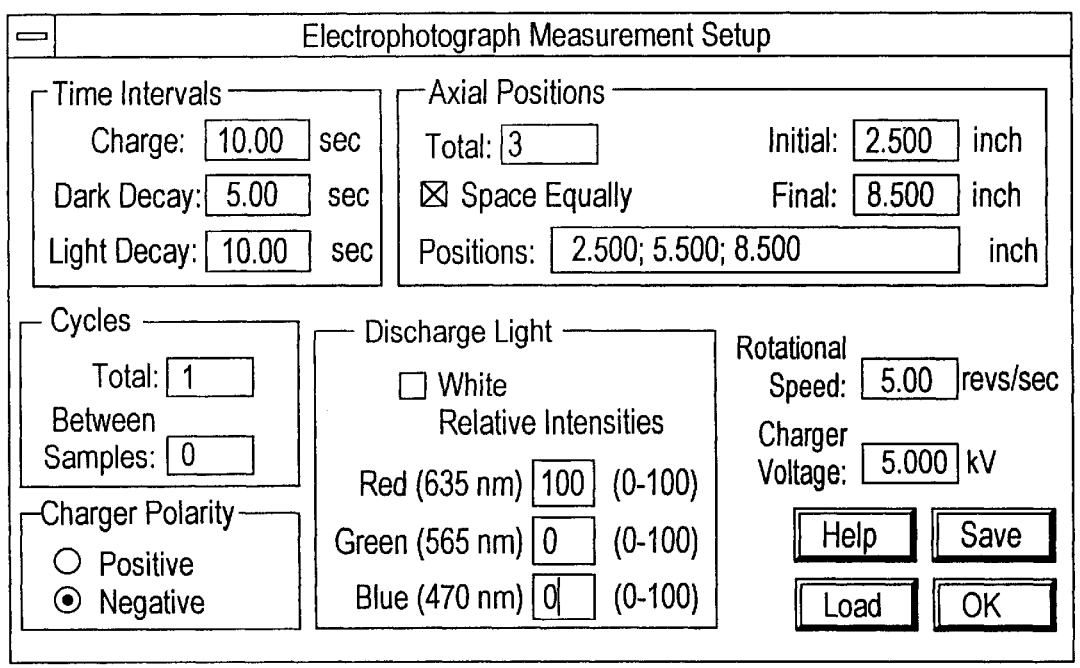
FIG. 9 is a depiction of a parameter selection display for the electrophotographic performance test of FIG. 2, provided by the user interface of the control software for the control unit of FIG. 1.

FIG. 9 is a depiction of a parameter selection user interface display for an exemplary electrophotographic measurement test, wherein measurements are taken by the high voltage probe 34 at 2.500 inches from a reference point, at 5.500 inches, and at 8.500 inches from the reference point. The drum 10 will be rotated at a speed of 5.00 revolutions per second. The charging device 26 is set at a 5.000 kV charging voltage for 10 seconds to the drum 10 followed by a dark decay of 5 seconds and a light decay of 10 seconds. The test will typically cycle plural times through the sequence of steps 102–112 for each report. Red light at maximum intensity (100%) will be used to discharge the drum 10. After making any corrections to the parameters, the system operator accepts the test parameters in step 70, and initiates the test 100 in step 72.

Figure 10:
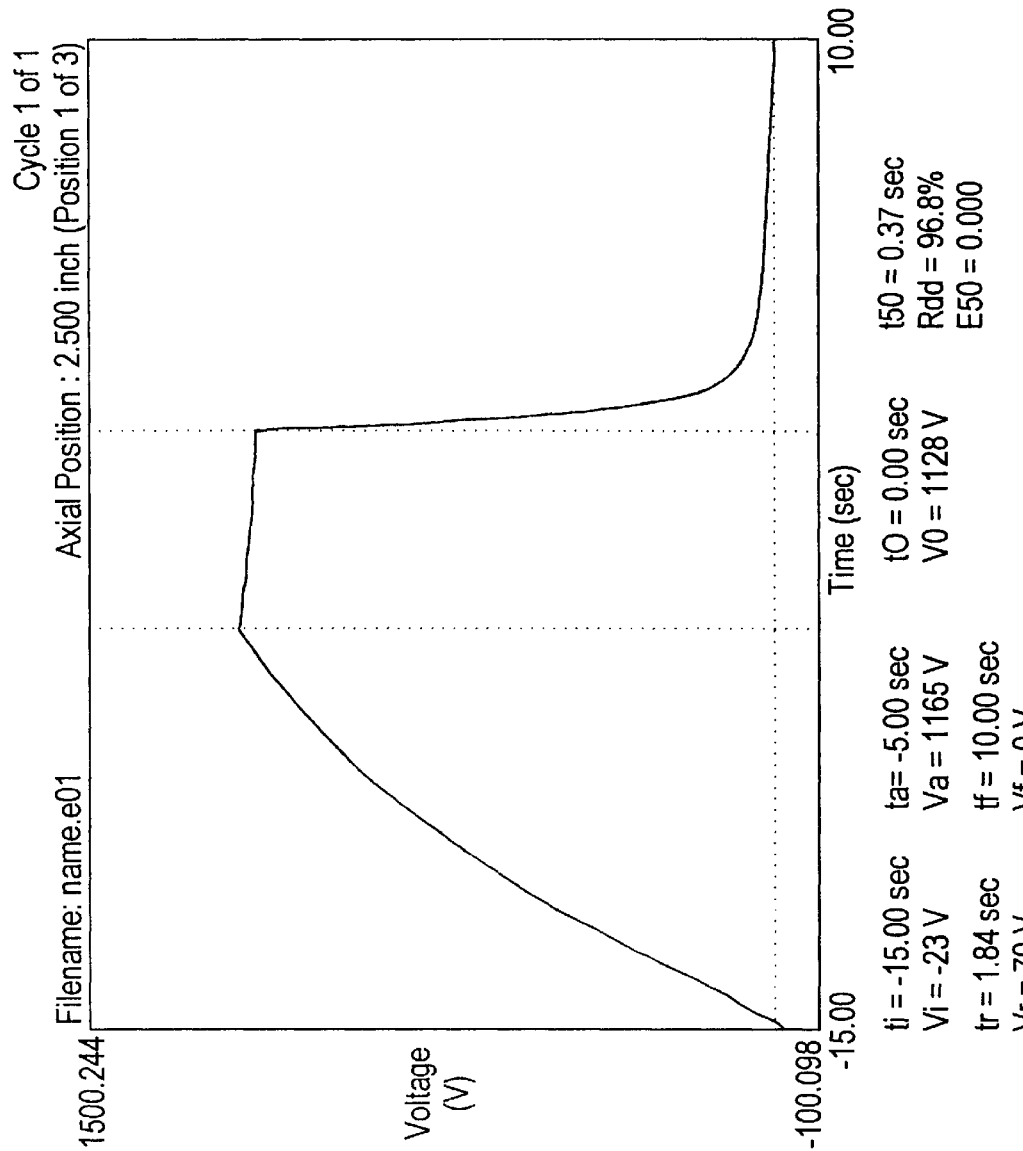
FIG. 10 is a graphical representation of the results of the electrophotographic performance test of FIG. 2.

FIG. 10 is a graphical representation of results of one location for a typical electrophotographic measurement test, in this case a location 2.500 inches down the drum. When the test is initiated at "$t_i$" time, an initial (pre-charging) voltage measurement "$V_i$" 102 is made.

The charging device 26 then imparts the selected charge in step 104 to the drum 10 for the predetermined time interval of 10 seconds, during which time the drum surface potential is continuously measured and recorded. At time "$t_a$", marking the conclusion of the charging step 104, the drum surface potential which indicates the level of charge acceptance is donated as "$V_a$" 106. The charged drum 10 is then left in the completely light-proof cabinet 14 for the selected dark decay time interval of 5 seconds, while the surface potential is continuously measured and recorded. At time "$t_o$", marking the conclusion of the dark decay step 108, the drum surface potential is denoted as "$V_o$", the drum 10 is then illuminated in step 110 with the selected light and source 38 for the selected light decay interval of 10 seconds, while the surface potential is continuously measured and recorded. Various key parameters are determined in step 112: the time elapsed for the illuminated area to discharge fifty percent is denoted as "$t_{50}$"; the residual surface potential is denoted "$V_r$" and is defined as the surface potential at time "$t_r$", which is at five times $_{50}$ relative to $t_o$. Finally, the time at the completion of light discharge is denoted as "$t_f$" and the surface potential at that time is denoted as "$V_f$". Other key parameters can be defined and calculated, such as "$R_{dd}$", the percentage of acceptance voltage retained during dark decay, defined as $V_o$ divided by $V_a$. The entire test sequence can be repeated at the same location for any desired number of times and/or at other drum locations.

In addition to the scanning techniques described above that employ a single probe to measure contact or surface potential of the photoreceptor, it is also possible to use two probes simultaneously to accelerate data collection and to further enhance the accuracy of the tests.

Figure 11:
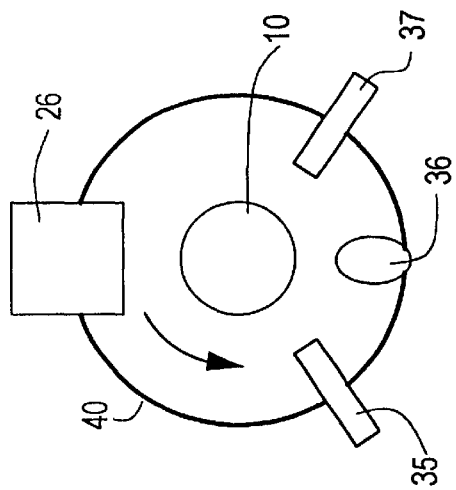
FIG. 11 is a top view of an alternative instrumentation configuration for the test system of FIG. 1A.

Referring to FIG. 11, a two probe configuration for the test station 12 is shown in a top view. In this configuration, a charge measurement probe 35 and a discharge measurement probe 37 are mounted on the carrier 40 with the first light source 36 interposed between them. As the drum 10 rotates in the direction indicated by the arrow, a region of the drum is charged by the charging device 26. Next, the charge held by the drum in that region is measured by the probe 35, following which a region of the drum is discharged by the first light source 36. Immediately thereafter, the effectiveness of the discharge in the target region is measured by the discharge measurement probe 37. The above described sequence enables a 360° scan of the drum 10 to be performed in fractions of a second, after which the carrier 40 is commanded to displace a predetermined increment along the axis of the drum 10, wherein the scanning sequence is continued. The above described helical scan enables electrophotographic measurements to be taken over the entire surface of the drum or selected regions very rapidly for processing to evaluate the photoreceptor.

Figure 12:
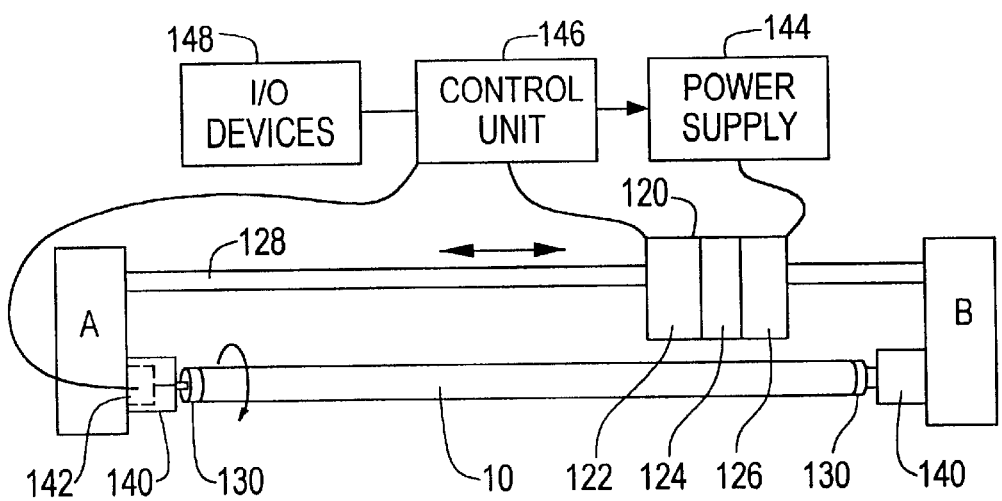
FIG. 12 is a perspective view of another embodiment of the test system of FIG. 1A.

FIG. 12 illustrates yet another configuration of the test station 12, wherein an instrumentation cluster 120 including at least one measurement probe 122, a discharge light source 126, and a charging device 126 moves linearly on a track 128 aligned parallel with and in close proximity to a photoconductive drum 10. The track 128 is movable to allow adjustment for accommodating drums of different diameters. The drum 10 has end-caps 130 by which a mandrel 140 retains the drum 10 in position for testing. The mandrel 140 is coupled to a motor 142 that rotates the drum 10 either continuously or incrementally in an indexed manner. A reversible polarity power supply 144 energizes the instrumentation cluster 120, which along with the power supply 144 and indexing motor 142 are responsive to a control unit 146, such as a microprocessor or computer. The control unit is responsive to operator input from input devices known in the art and presents control options and test results on output devices known in the art, these devices referred to collectively as I/O devices 148.

The measurement principals used by the test station illustrated in FIG. 12 are the same as those described hereinabove with respect to the test station of FIG. 1A. However, the tests are performed in a slightly different manner due to the configuration of the instrumentation cluster 120. For example, as the instrumentation cluster 120 moves from block A toward block B, the charging device 126 imparts a charge to the drum 10 which is immediately evaluated by the measurement probe 122. The drum 10 is then held stationary while the instrumentation cluster 120 returns to a starting point proximate block A from which a subsequent scan toward block B is recommenced. In the subsequent scan, the discharge light source 124 is activated to discharge the drum 10, the discharge of which is immediately evaluated by the measurement probe 122. In another embodiment, the charging device 126 is adjacent a charge measurement probe, adjacent to a light source, adjacent to a discharge measurement probe, allowing a complete test to be performed in a single linear scan.

Although the drum 10 can be rotated and scanned until the drum 10 has been evaluated through 360° of rotation, tests have revealed that because degradation is largely the same around the drum at each axial displacement evaluation of a single linear scan is often sufficient to make an accurate useability determination for the drum 10. Therefore, because the drum does not need to be rotated, the motor 142 can be eliminated without adversely affecting test results. Elimination of the motor combined with a concomitantly simplified retaining structure for the drum and the compact configuration of the instrumentation cluster 120, results in a test station markedly smaller, lighter, and less expensive than prior art devices which are unable to perform the battery of tests performed by the present invention. Accordingly, the entire test station illustrated in FIG. 12, is transportable to a user or other site by a maintenance technician.

If full drum testing is desired, the drum is rotated a fixed angle (e.g. 10–30°) after the linear scan, and a new scan generated.

Figure 13:
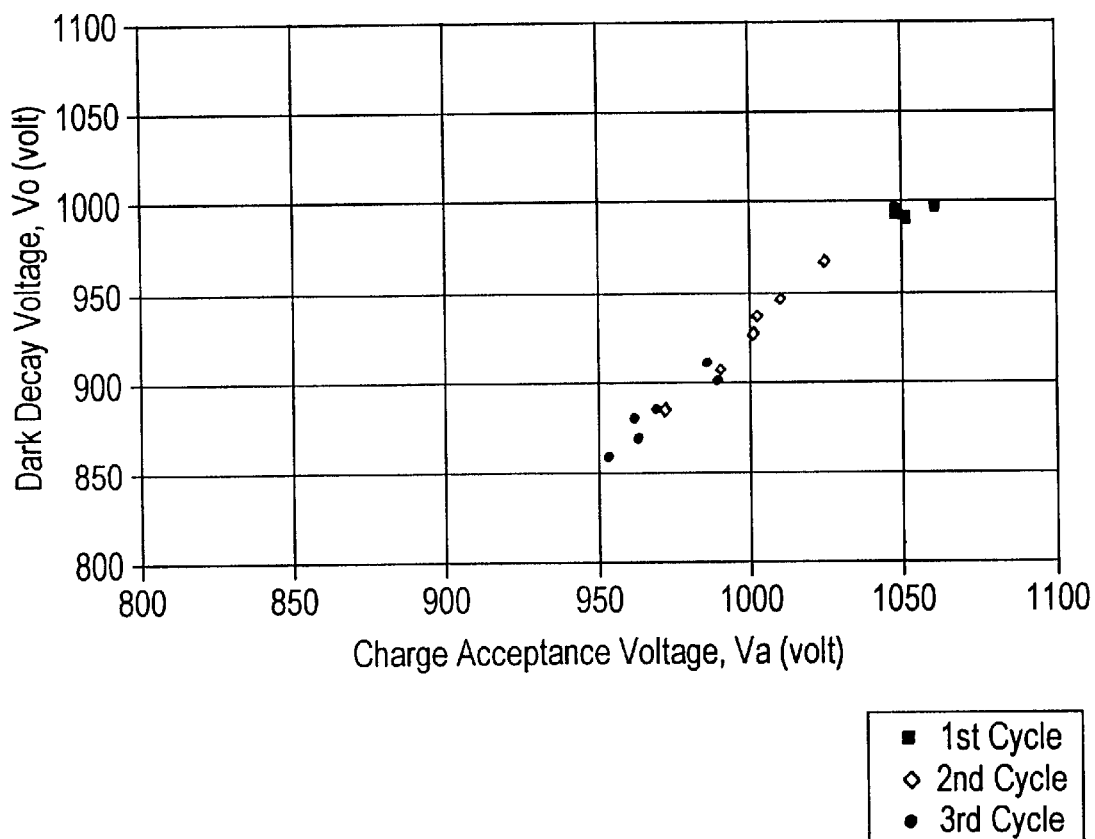
FIG. 13 is a graphical representation of life cycle testing results performed with the test system of the invention.

The test system of the invention permits life cycle testing of photoconductors which degrade over time. FIG. 13 is a graphical depiction of the dark decay voltage versus the charge acceptance voltage for six photoconductors of the same type over three cycles of use at the indicated test voltages. For convenience, one cycle is defined as using the same photoconductor to print 3,000 standard sheets of paper. Another way to track cycles is one cycle per toner cartridge for a typical laser printer. As can be determined from the graph, the photoreceptors degrade in a fairly consistent manner from cycle to cycle. This enables a test system operator to test a photoreceptor having an unknown or unmonitored use state and compare it to the test results for a similar type photoreceptor to determine its cycle age and life remaining. For a photoreceptor at a known cycle, the test results indicate whether the photoconductor is aging properly. Thus, the system software enables an operator to compare test results of a tracked photoreceptor with its stored life history or to compare test results of an untracked photoreceptor with a stored calibration curve for that type of photoreceptor. The operator can also input the level of performance degradation acceptable to a particular photoreceptor application or user which is compared to the drum being tested to establish a simple pass-fail test output.

Figure 14C:
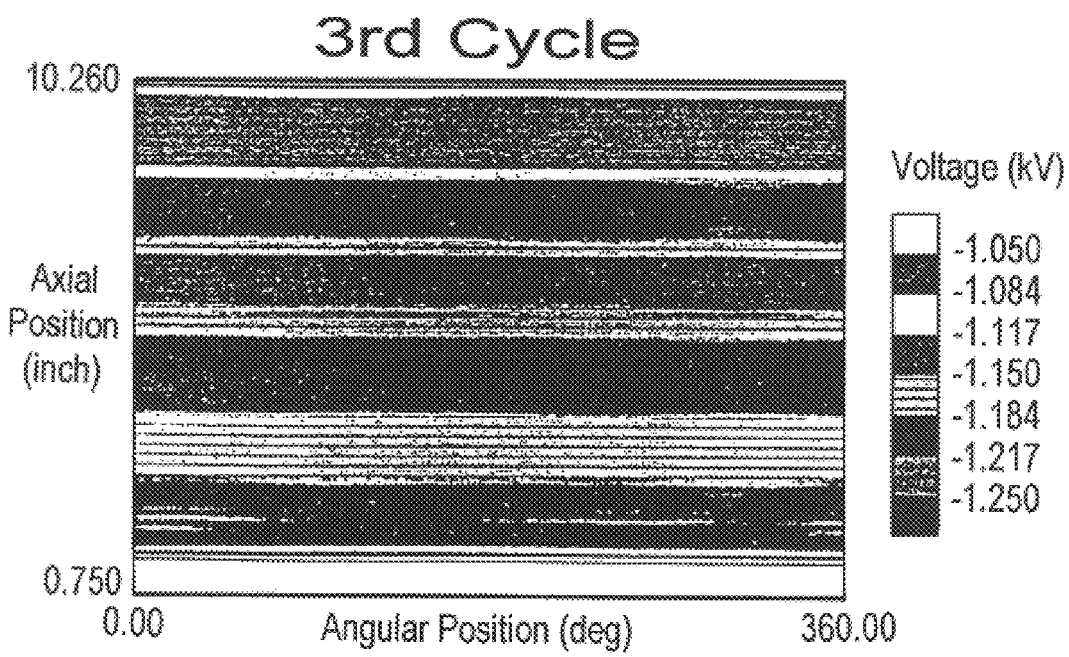
FIG. 14C is a graphical representation of defect mapping test results of a photoreceptor after a second usage cycle.
Figure 14A:
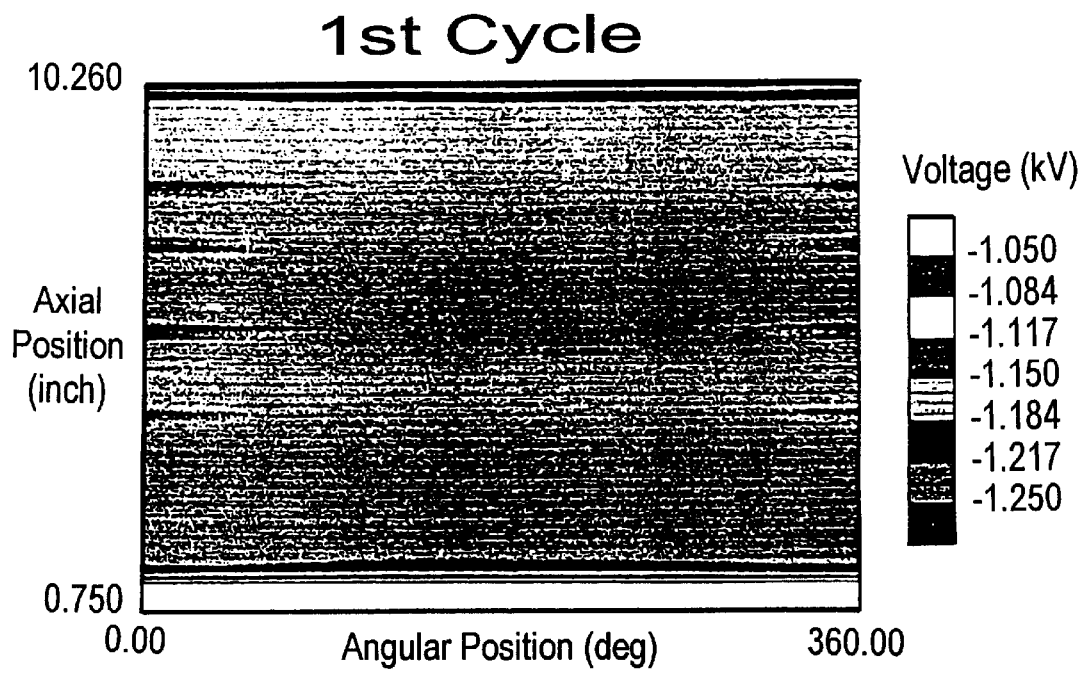
FIG. 14A is a graphical representation of defect mapping test results for a photoreceptor after a first usage cycle.
Figure 14B:
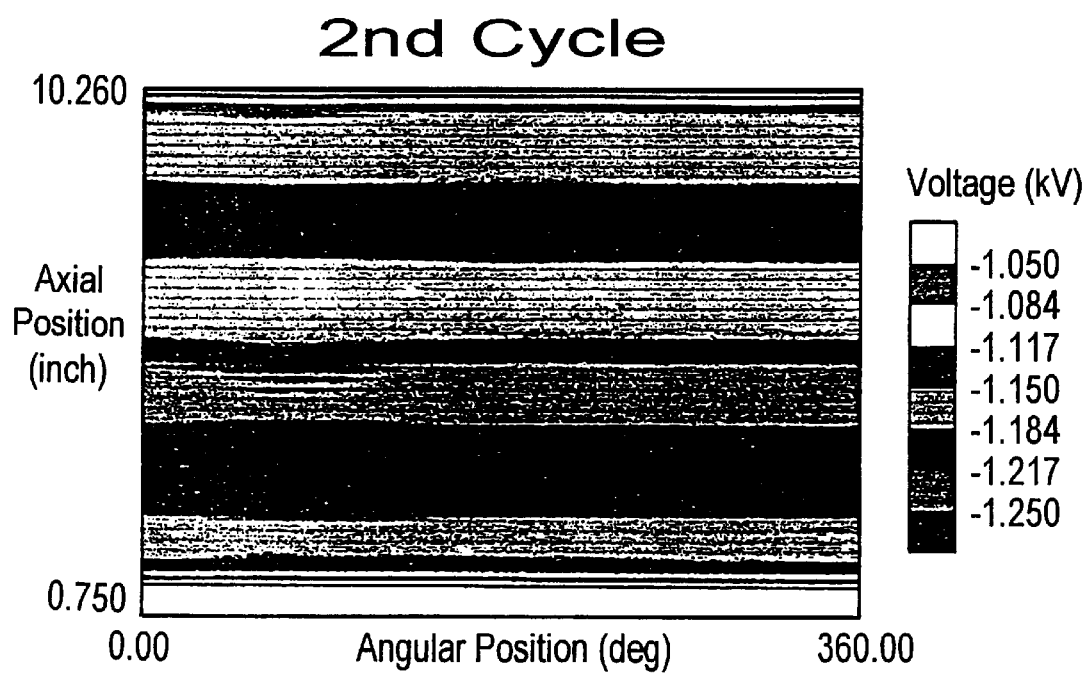
FIG. 14B is a graphical representation of defect mapping test results for a photoreceptor after a second usage cycle.

Referring now to FIGS. 14A, 14B, and 14C, graphical illustrations are shown corresponding to a first cycle (new drum), a second cycle (slightly used drum), and a third cycle (more heavily used drum), respectively. As with the graphs of FIGS. 4, 6 and 8, the graphical output can be gray scale or colored to represent voltages or defects at various points or regions on the photoreceptor. It should be noted that the voltage values for a 360° scan of a drum are generally consistent at a given axial position. Thus, although a full 360° scan provides a very accurate representation of an entire drum, an axial scan taken at any given angular position provides adequate data for life cycle predictions to be made, as described with respect to the test station illustrated in FIG. 12.

Figure 15A:
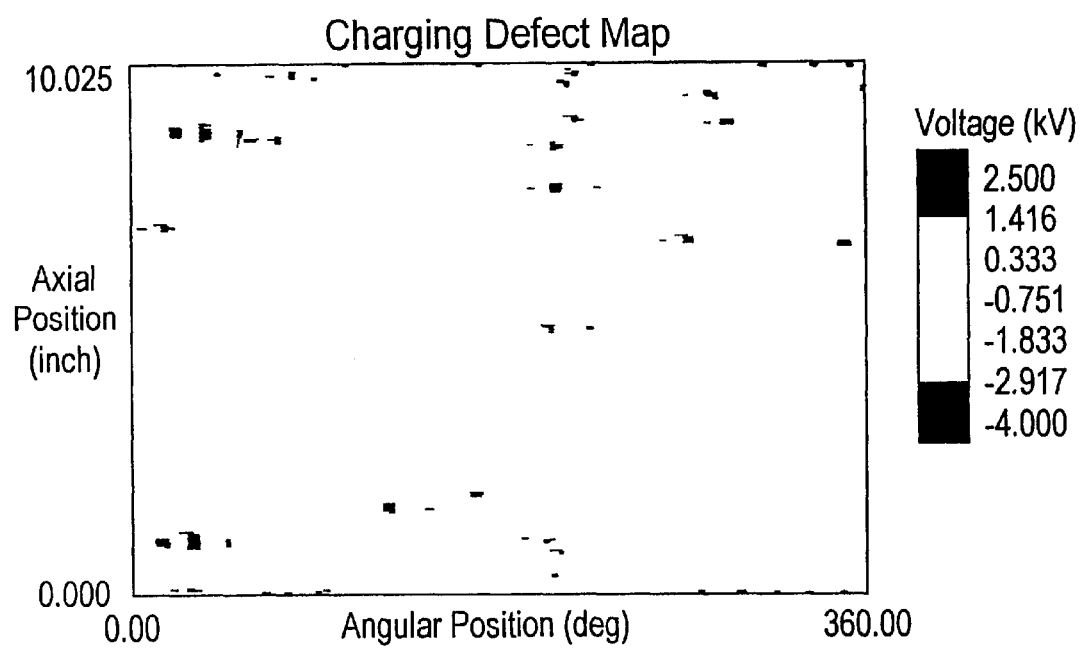
FIG. 15A is a graphical representation of a charging defect map.
Figure 15B:
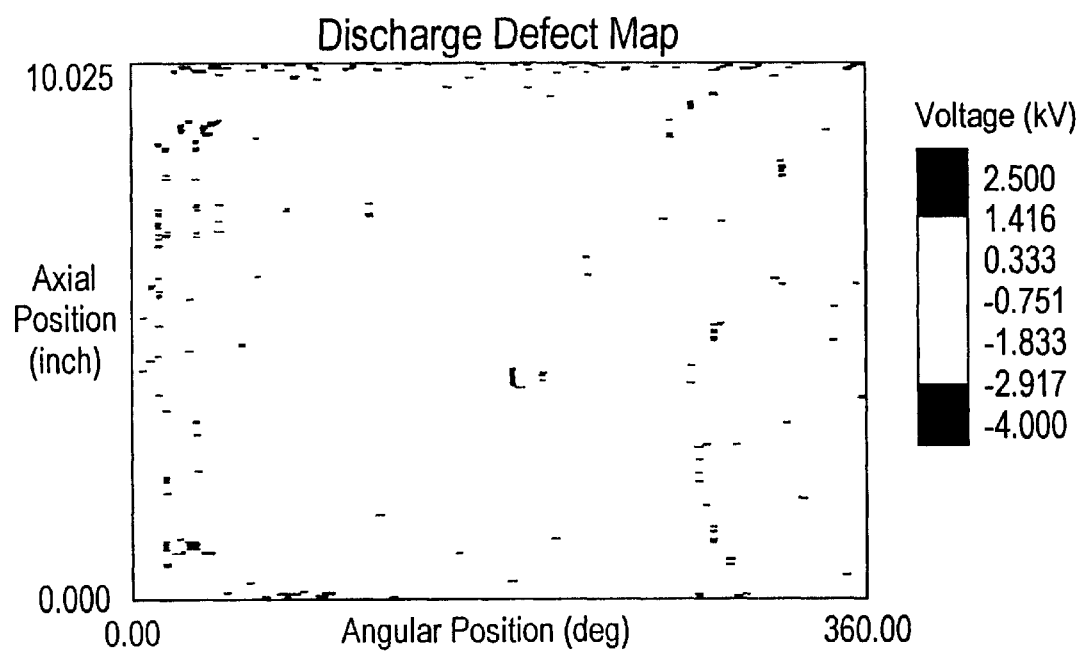
FIG. 15B is a graphical representation of a discharge defect map.

The flexibility of the software also allow an operator to select for display only user defined significant voltage values, such as those indicated on the charging defect map of FIG. 15A and on the discharge defect map of FIG. 15B.

Figure 16A:
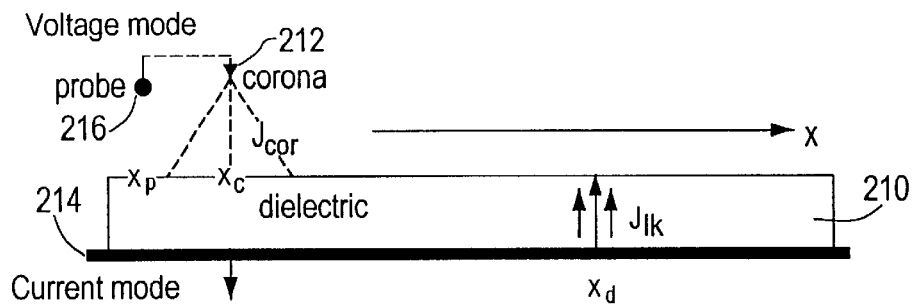
FIGS. 16A and 16B illustrate the use of the invention with generalized substrates and with current as well as voltage testing procedures.

While the invention described above has been described with respect to the use of the test system for xerographic drums and the like, it is to be appreciated that the invention can be used or modified as described below for use with other dielectric materials with varying dielectric relaxation rates. Examples of such material without limitation include paper, transparency and other media as well as charge, development, transfer or fuser rollers. The system is thus usable for the testing of many materials where the dielectric relaxation rate and its consistency throughout the material are important to the materials proper functioning. Accordingly, in a generalized form of the invention as shown in FIG. 16A, a dielectric substrate 210 of a material to be tested to which a scanning corona charging head 212 applies a charge, relative to a support 214 (typically grounded), which is then read by a probe 216 all as described above in a particular implementation. The remaining charge sensed by the probe is detected and may also be mapped as described above. The substrate can then be in any form that it is desired to test for dielectric relaxation.

Figure 16B:
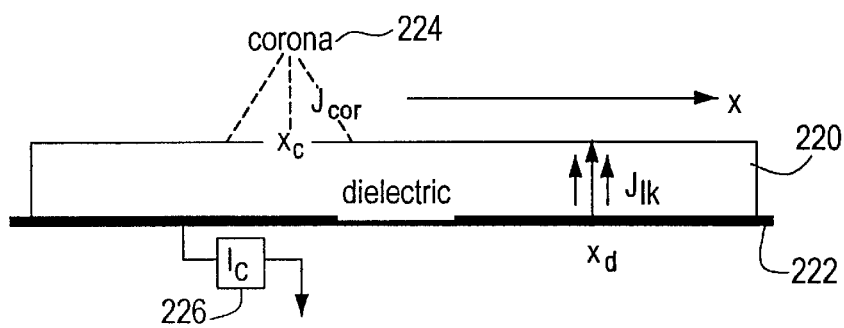

While the system described above has used a corona source to charge a substrate under test and subsequently read out the remaining voltage, it is possible to sense a current flow rather than a remaining voltage at the substrate for testing its dielectric relaxation properties. FIG. 16B illustrates such a system in which a substrate 220 is backed by a conductive support 222. In the examples above, the substrate 220 and backing 222 are xerographic rollers. A corona head 224 applies electrical energy to the substrate 220 while a current sensor 226 detects the current applied by the corona at each point along the substrate during the scanning of the head 224.

TABLE I

II. Features of Defect Signals
II-A. voltage Mode
1. Width of signal (note: width refers to that in the scan direction)
$\Sigma$ increases with the width of the voltage probe
$\Sigma$ is of the order of, or larger than the width of voltage probe.
$\Sigma$ increases as the distance between the corona device and voltage probe increases
$\Sigma$ increases as the scan speed decreases (latter two are consequences of lateral conduction)
2. Depth of signal
$\Sigma$ increases as the probe width decreases
$\Sigma$ increases linearly as the defect width increases
$\Sigma$ increases superlinearly as the nominal surface voltage increases
$\Sigma$ increases as the corona width increases, especially at high speeds
$\Sigma$ increases as the scan speed decreases (with a limit) (also from lateral conduction)
3. Signal corresponds to the voltage at a time delay after corona charging, that is determined by the corona-probe separation and the scan speed.
4. The above features are common to both insulating and semi-insulating (relaxable) rollers.
II-B. Current Mode
1. Width of signal
$\Sigma$ increases with the corona width
$\Sigma$ is of the order of the width of corona
$\Sigma$ increases as the scan speed decreases (a consequence of lateral conduction)
2. Depth of signal
$\Sigma$ increases linearly as the defect width increases TABLE I-continued Σ increases as the corona width increases, especially at high speeds
Σ increases as the scan speed decreases (with a limit). (also from lateral conduction)
3. Signal corresponds to the charging current when the corona center is at the defect center.
4. The above features are common to both insulating and semi-insulating (relaxable) rollers. In the semi-insulating (relaxable) rollers, the signal-to-noise ratio is small.

Figure 17:
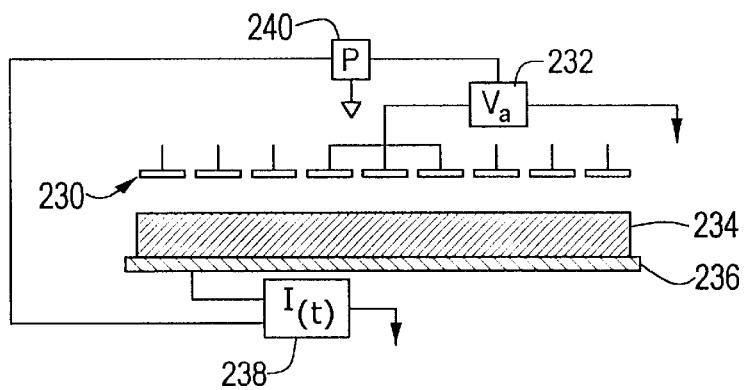
FIG. 17 illustrates an embodiment of the present invention using an array for applying current to a test substrate.
Figure 18:
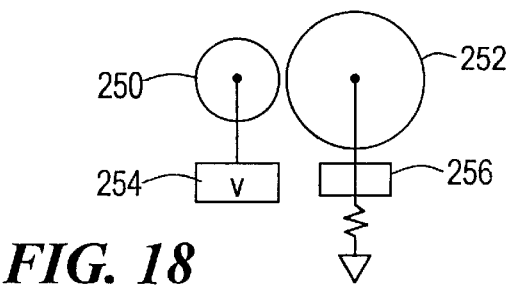
FIG. 18 illustrates an embodiment of the present invention using a wire or roller to apply current to a test substrate.

FIGS. 17 and 18 illustrate different approaches to the application of a current signal to a substrate being tested. An alternative to the Electrostatic Charge Decay (ECD) method shown with respect to FIGS. 1–15 of defect mapping for semi-insulating rollers is schematically illustrated in FIG. 17. The corona and voltage probe assembly of ECD is replaced by an array of micro-electrodes spanning a partial or the full length (or circumference) of the roller, and located a small air gap (about 100 microns) from the roller surface. A high voltage (<1000 V, less than the Paschen voltage for the air gap) is applied to a few electrodes ("on-electrodes") at a time. The total current I(t) is monitored as the on-electrodes travel down the length (or circumference) of roller. At anytime, I(t) is the sum of the transient currents from the roller area under the on-electrodes. As the on-electrodes encounter a defect, the detected I(t) changes from the normal value to a larger or smaller value according to whether the defect causes more or less charge injection. If the defect-width is less than or equal to the width of a single electrode, the signal width increases with the width (or number) of the on-electrodes, but the signal-to-noise ratio decreases as the on-width increases. For defects with a width larger than the single electrode width, the magnitude and the width of signal, and the signal-to background ratio increase with the defect width. The time duration the electrodes are turned on (on-time) must be longer than the current rise-time. The latter is in general of the order of or longer than the transit times. Therefore, the scan speed is limited by the transit time, i.e. by the charge mobility. For roller materials of practical interest, a upper limit of scan speed is estimated to be several hundred cm/sec.

The advantages over the conventional ECD method are (1) the elimination of corona pre-charging; (2) the lower cost of current detector (vs. for voltage); (3) No moving detector if a full-length array is used.

In the example of FIG. 17, an array of electrodes, either linear or two dimensional, 230 are driven by a voltage source 232. The array 230 is placed adjacent to a substrate 234 on a support 236, and current is sensed by a sensor 238. The array can be placed close enough to the substrate to transfer charge, or can be driven with a pulsed or AC current by source 232. Typically the source will multiplex the current to the array to cause a scanning function and allow the sensed current to be correlated to position by a processor 240 for mapping as described above.

FIG. 18 illustrates a variation on this concept using a conductive roller or wire electrode 250 placed in close proximity with a dielectric roller drum 252. Voltage is applied to the drum 252 from a source 254 and the resulting current sensed by a current sensor 256. This system can be used to provide a fast go/no-go testing of drums or other substrates.

This alternative to the micro-electrode array concept uses an electrode which spans a partial or the full length (or circumference) of the roller, and is located a small air gap (about 100 microns) from the roller surface. A high voltage (<1000 V, less than the Paschen voltage for the air gap) is applied to the electrode. If a defect, particularly a pinhole or scratch type of defect passes underneath the electrode, it can be detected in a variety of ways including: 1) a surge in the current, 2) electromagnetic noise, 3) low level audible or ultrasonic noise, or 4) light emission, mostly in UV. The electrode can be stationary or rotating synchronously with the dielectric roller.

The advantage of the method is that it is a rapid scanning method for the detection of defects (since it only requires a unidirectional scanning).

Figure 19A:
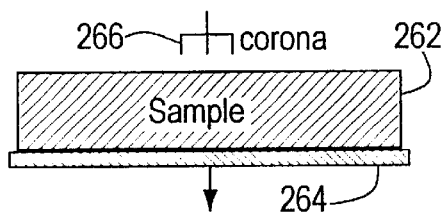
FIGS. 19A–19E illustrate embodiments of the invention using insulating layers to separate out boundary effects from bulk material effects.
Figure 19B:
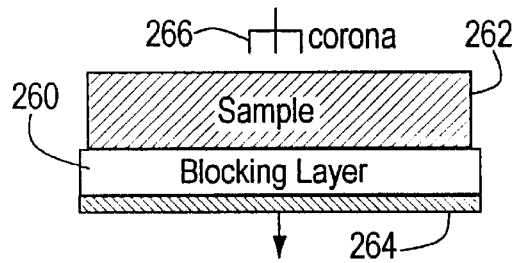
Figure 19C:
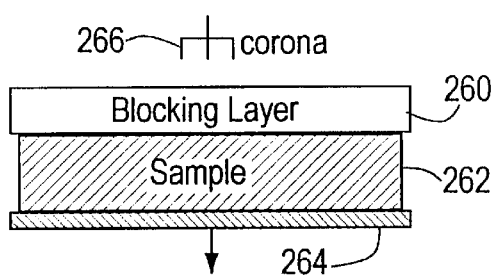
Figure 19D:
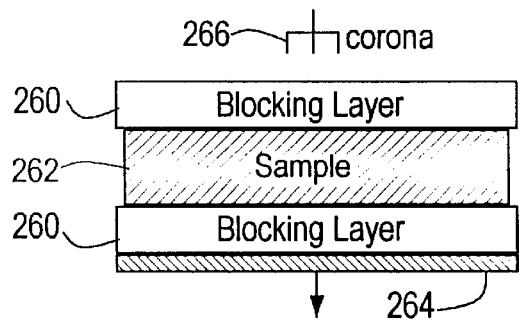

A further embodiment and variation of the ECD method of FIG. 19A is described with respect to FIGS. 19B–19E. A charge-blocking layer 260 (a perfect insulator, like MYLAR or TEFLON) is inserted between the sample substrate 262 and the substrate support electrode 264 and/or the corona source 266, or both as schematically shown below in FIGS. 19 B, C, and D.

The dielectric relaxation process involved in the defect mapping by the ECD depends on the charge either injected from the boundaries (surface and/or substrate), or generated in the sample bulk. Thus, comparisons of data obtained with blocking layers (FIGS. 19B–19E) and those with the conventional method (FIG. 19A) serve to identify the source of excess or insufficient charge or voltage associated with the defects. Although the configuration with a blocking layer 260 between the sample and substrate, cannot be applied (for non-destructive testing) to samples already coated on a roller shaft, it is useful in mapping isolated dielectric material such as loose sheets of transfer media, such as paper. A reversal of corona ion polarity can add to the information on the charge species.

Figure 19E:
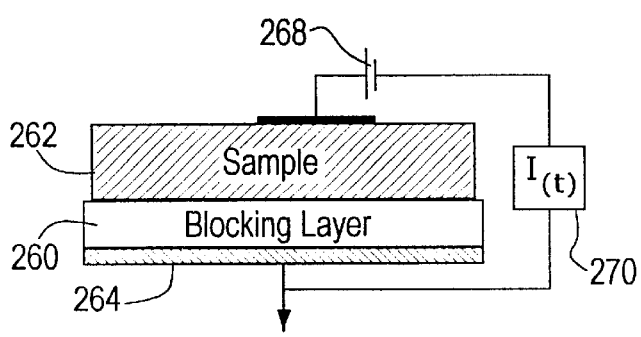

The corona source 266 in (in FIGS. 19B, C, and D) can be replaced by a voltage source 268 as shown in FIG. 19E. In an embodiment the voltage source 268 is variable and data is taken at several voltages due to the variation of response with voltage. The transient current sensed in sensor 270 as a function of time can be used to determine dielectric relaxation properties such as charge density and charge mobility by known relationships.

The earlier embodiments describe the detection of defects that are of electrical nature, such as abnormal charge injection, or "leakage currents". This embodiment allows techniques that are equally effective in detection of other types of defects, for example, those which arise from film thickness variation. In the case of film thickness variation, the film capacitance, $C_f$, is the ratio of the permitivity to the thickness. Thus, a variation in thickness results in a variation in the capacitance. The total current $I_T$ that flows through the electrode circuit can be written as, $I_T=[I_{cond}]av/(1+C_f/C_a)$, where $[I_{cond}]$ av denotes the integral of the conduction current over the film thickness divided by the film thickness, and $C_a$ is the capacitance of the air-gap or the blocking layer. Therefore, a change in film thickness is reflected in the current signal. In the open-circuit, voltage mode of detection, (FIGS. 19A–19D), the surface voltage V is given by: $V=Q/C_T$, where Q is the charge deposited on the surface and $C_T$ is the total capacitance. In the conventional ECD case (FIG. 19A), $C_T=C_f$, and in the cases with blocking layers (FIGS. 19B, C and D), $C_T=C_fC_b/(C_f+C_b)$, where $C_b$ is the capacitance (or combined capacitance for 4D) of the blocking layer(s). By using a thin blocking layer, $C_b$ can be made large compared to $C_f$. Then, $C_T$ is nearly equal to $C_f$, and the film thickness variation can be directly reflected in the voltage signal.

Data obtained from these other embodiments can like data described with respect to FIGS. 1–15 be graphically presented in map form as described above.

Although the invention has been shown and described with respect to exemplary embodiments thereof, various other changes, omissions and additions in form and detail thereof may be made therein without departing from the spirit and scope of the invention.

What is claimed is:

1. A dielectric material test system comprising:
   a dielectric material support adapted to receive a dielectric material;
   one or more electrodes adapted to apply electrical energy from a source to a two dimensional area adjacent said dielectric material support for storage by said dielectric material;
   a sensor for the electrical energy stored in said dielectric material and providing an output representation of the dielectric relaxation of the dielectric material in response to the stored energy over said two dimensional area; and
   a blocking layer provided between said dielectric material support and said one or more electrodes, wherein said sensor is adapted to sense charge transport over said two dimensional area.

2. The system of claim 1 where said dielectric material is paper or other media.

3. The system of claim 1 wherein said one or more electrodes are adapted to apply said electrical energy as an electric current.

4. The system of claim 1 wherein said one or more electrodes comprise a roller or wire and said support is a drum.

5. The system of claim 1 wherein said one or more electrodes comprise an array of electrodes and said source is adapted to simultaneously apply said electrical energy to said array via one or more array electrodes.

6. The system of claim 1 wherein said blocking layer is provided in one of the configurations consisting of between said dielectric material and said one or more electrodes, between said dielectric material and said dielectric material support or combinations thereof.

7. The system of claim 6 wherein said one or more electrodes applies said electrical energy to said dielectric material as a current.

8. A dielectric material test system comprising:
   a dielectric material support adapted to receive said dielectric material;
   one or more electrodes adapted to apply electrical energy from a source to a two dimensional area adjacent said support for storage by said dielectric material, wherein said one or more electrodes are adapted to apply said electrical energy as an electric current; and
   a sensor for the electrical energy stored in said dielectric material and providing an output representation of the dielectric relaxation of the material in response to the stored energy over said two dimensional area.

* * * * *

UNITED STATES PATENT AND TRADEMARK OFFICE
CERTIFICATE OF CORRECTION

PATENT NO.     : 6,469,513 B1
DATED          : October 22, 2002
INVENTOR(S)    : Ming-Kai Tse It is certified that error appears in the above-identified patent and that said Letters Patent is hereby corrected as shown below:

Column 1,
Line 13, "1993 which" should read -- 1993 (now abandoned) which --;

Column 10,
Line 7, "$_{50}$" should read -- $t_{50}$ --;

Column 12,
After line 37, prior to TABLE 1, insert the following -- Table 1 below illustrates the differences and advantages of the use of voltage or current readout. --;

Column 14,
Line 52, "$I_T=[I_{cond}]av/ (1+C_f/C_a)$," should read -- $I_T= [I_{cond}]_{av}/ (1+C_f/C_a)$, --; and
Line 53, "$[I_{cond}]$ av" should read -- $[I_{cond}]_{av}$ --.

Signed and Sealed this

Seventh Day of October, 2003

JAMES E. ROGAN
*Director of the United States Patent and Trademark Office*